(12) United States Patent
Jeong et al.

(10) Patent No.: US 10,737,556 B2
(45) Date of Patent: Aug. 11, 2020

(54) PHOTOCATALYTIC MODULE FOR AUTOMOBILE AIR CONDITIONER AND AUTOMOBILE AIR CONDITIONER HAVING THE SAME

(71) Applicant: SEOUL VIOSYS CO., LTD., Ansan-si (KR)

(72) Inventors: Jae Hak Jeong, Ansan-si (KR); Sang Cheol Shin, Ansan-si (KR); Ji Won Kim, Ansan-si (KR); Woong Ki Jeong, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 177 days.

(21) Appl. No.: 15/534,952

(22) PCT Filed: Dec. 14, 2015

(86) PCT No.: PCT/KR2015/013673
§ 371 (c)(1),
(2) Date: Jun. 9, 2017

(87) PCT Pub. No.: WO2016/093677
PCT Pub. Date: Jun. 16, 2016

(65) Prior Publication Data
US 2017/0334267 A1    Nov. 23, 2017

(30) Foreign Application Priority Data

Dec. 12, 2014 (KR) .................. 10-2014-0179706
Jun. 30, 2015 (KR) .................. 10-2015-0093755

(51) Int. Cl.
*B60H 3/06* (2006.01)
*A61L 9/20* (2006.01)
(Continued)

(52) U.S. Cl.
CPC ........... *B60H 3/0658* (2013.01); *A61L 9/205* (2013.01); *B01D 53/8687* (2013.01);
(Continued)

(58) Field of Classification Search
CPC .. B60H 3/0658; B60H 3/0085; B60H 3/0078; B60H 2003/0675; B01D 53/8687;
(Continued)

(56) References Cited

U.S. PATENT DOCUMENTS 8,535,426 B2 * 9/2013 Sadler .................. A23B 7/152
95/117
8,709,341 B2 * 4/2014 Day ........................ A61L 9/205
422/1

(Continued)

FOREIGN PATENT DOCUMENTS

CN    2918131 Y    7/2007
EP    1494880 B1    5/2006
(Continued)

OTHER PUBLICATIONS

English translation of FR2838379 (Year: 2003).*
(Continued)

*Primary Examiner* — Regina M Yoo
(74) *Attorney, Agent, or Firm* — Perkins Coie LLP

(57) ABSTRACT

The present invention relates to a photocatalytic module for an automobile air conditioner and an automobile air conditioner having the same and, more particularly, to a photocatalytic module capable of eliminating various germs resulting from dew formed on an evaporator installed in an automobile air conditioner and corresponding bad smell, and an air conditioner having the same.

The photocatalytic module includes a duct fixation frame 54 adjacent to an inner wall of the duct 10; a filter fixation frame 55 having one end connected to the duct fixation frame, the (Continued)

(a)

(b)

filter fixation frame 55 fixing the photocatalytic filter 52; a photocatalytic filter 52 fixed by the fixation frame 55, being formed by applying a photocatalytic material onto a supporter having a shape of a plurality of cells neighboring each other and provided with a plurality of airflow paths; and a substrate 58 fixed to the duct fixation frame 54 and equipped with an ultraviolet (UV) light emitting diode (LED) 59 for radiating ultraviolet light toward the photocatalytic filter 52. The present provides an air conditioner having the photocatalytic module installed therein and an LED disposed upstream of the photocatalytic filter on the flow path of the duct.

16 Claims, 10 Drawing Sheets

(51) Int. Cl.
| | | |
|---|---|---|
| | *B60H 3/00* | (2006.01) |
| | *B01D 53/88* | (2006.01) |
| | *F24F 3/16* | (2006.01) |
| | *B01D 53/86* | (2006.01) |

(52) U.S. Cl.
CPC ......... *B01D 53/885* (2013.01); *B60H 3/0078* (2013.01); *B60H 3/0085* (2013.01); *F24F 3/1603* (2013.01); *F24F 3/166* (2013.01); *A61L 2209/133* (2013.01); *A61L 2209/14* (2013.01); *A61L 2209/16* (2013.01); *B01D 2255/802* (2013.01); *B01D 2257/91* (2013.01); *B01D 2259/4566* (2013.01); *B01D 2259/804* (2013.01); *B60H 2003/0675* (2013.01); *F24F 2003/1667* (2013.01)

(58) Field of Classification Search
CPC ............ B01D 53/885; B01D 2259/804; B01D 2257/91; B01D 2259/4566; B01D 2255/802; F24F 3/1603; F24F 3/166; F24F 2003/1667; A61L 9/205; A61L 2209/133; A61L 2209/14; A61L 2209/16
See application file for complete search history.

(56) References Cited

U.S. PATENT DOCUMENTS

| | | | |
|---|---|---|---|
| 8,911,670 B2 * | 12/2014 | Wang | B01D 53/8668 |
| | | | 422/120 |
| 10,039,852 B2 * | 8/2018 | Yi | A61L 9/20 |
| 2004/0013583 A1 * | 1/2004 | Burkhardt | A61L 9/16 |
| | | | 422/186.3 |
| 2010/0260644 A1 * | 10/2010 | Day | A61L 9/205 |
| | | | 422/121 |
| 2011/0033346 A1 * | 2/2011 | Bohlen | A61L 9/205 |
| | | | 422/186.3 |
| 2017/0036516 A1 * | 2/2017 | Kim | A61L 9/205 |

FOREIGN PATENT DOCUMENTS

| | | |
|---|---|---|
| FR | 2838379 A1 | 10/2003 |
| JP | 2000-071742 A | 3/2000 |
| JP | 2001035287 A | 2/2001 |
| JP | 2001-158229 A | 6/2001 |
| JP | 2002-017837 A | 1/2002 |
| JP | 2002-253662 A | 9/2002 |

OTHER PUBLICATIONS

International Search Report and Written Opinion in International Application No. PCT/KR2015/013673, dated Feb. 23, 2016.
Extended European Search Report dated Jul. 31, 2018 in European Patent Application No. 15867708.8, 7 pages.

\* cited by examiner

[Fig. 1]
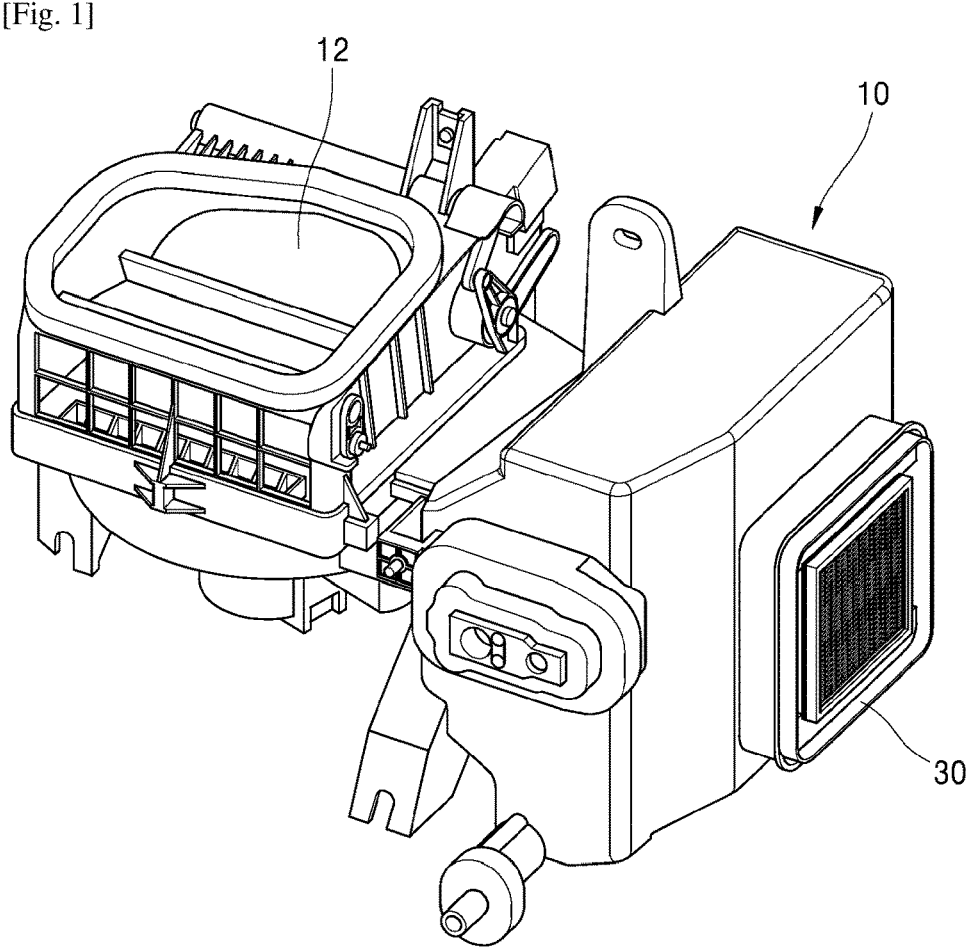
[Fig. 2]
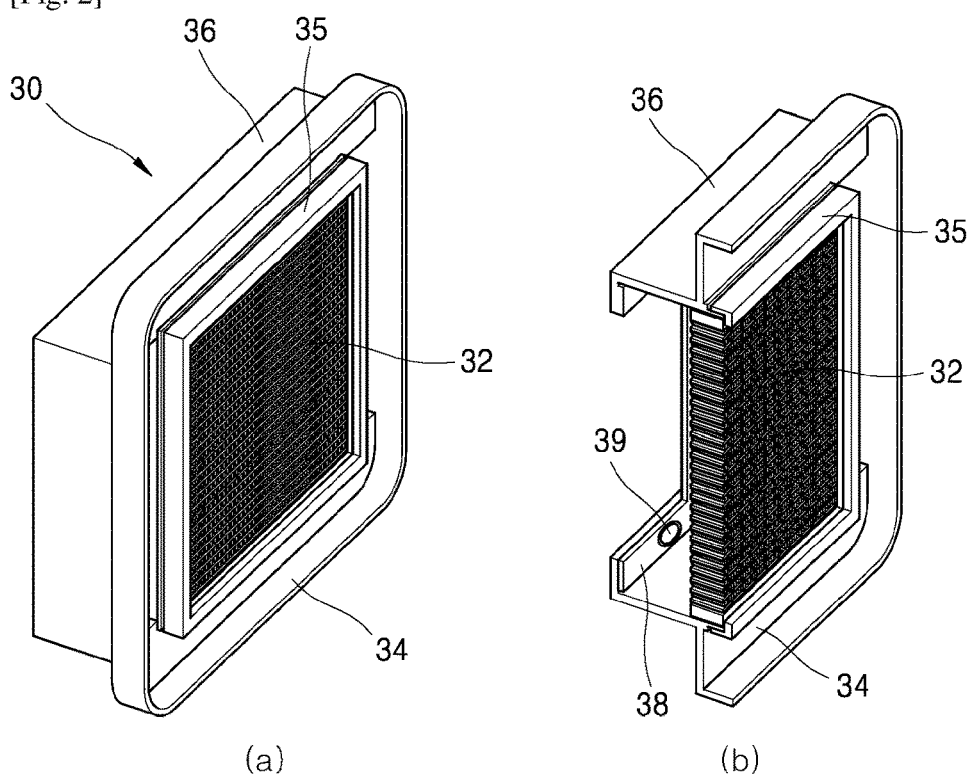
(a)  (b)

[Fig. 3]
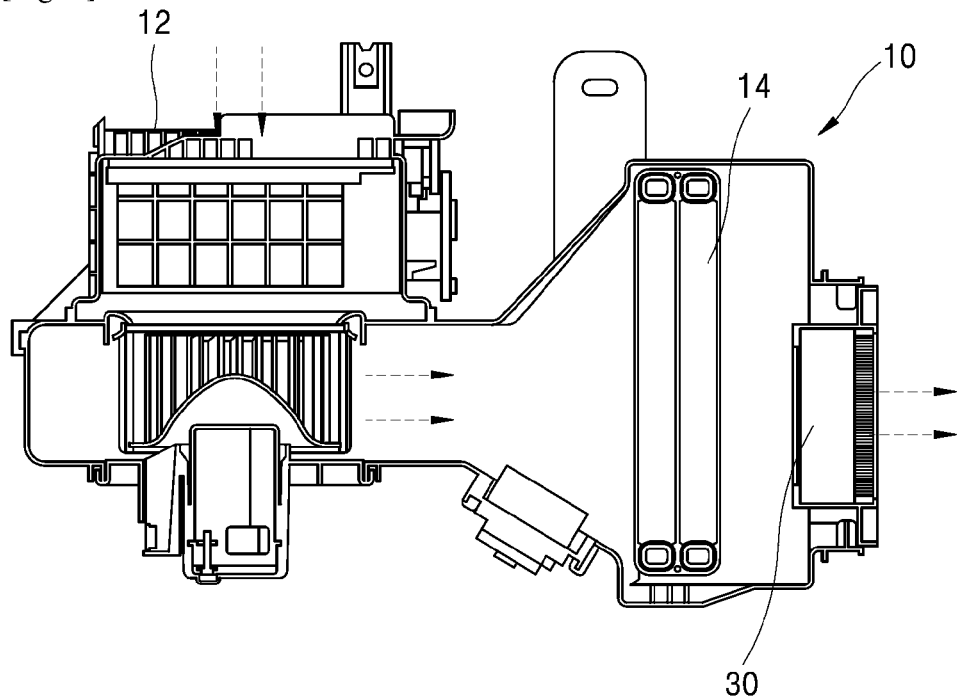
[Fig. 4]
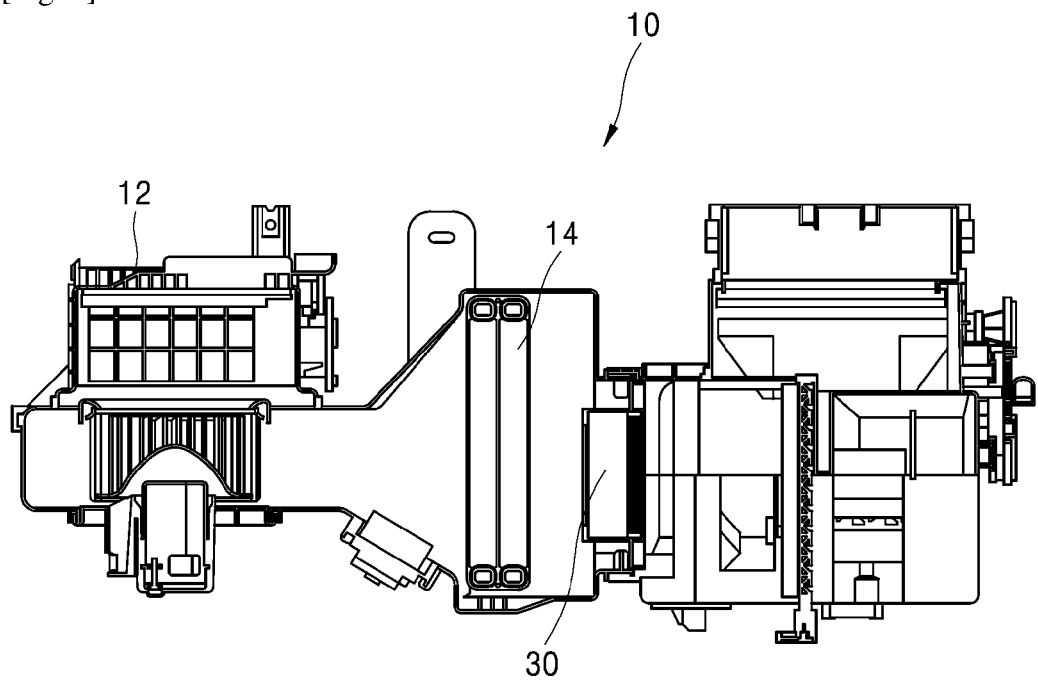

[Fig. 5]
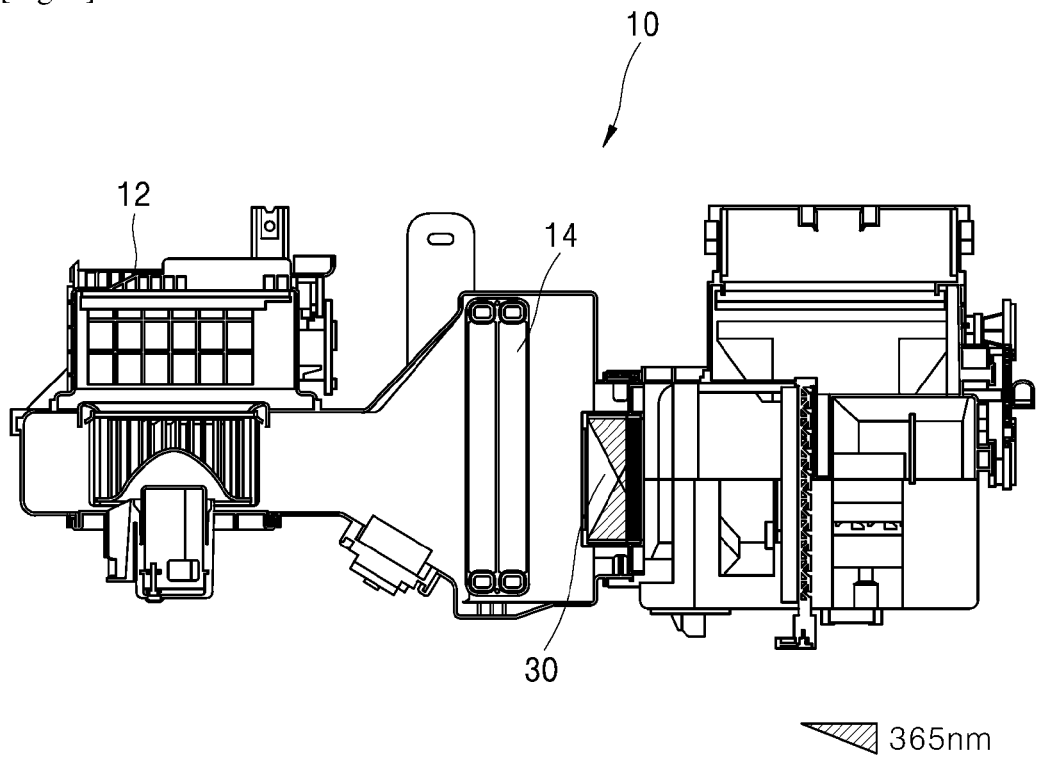
[Fig. 6]
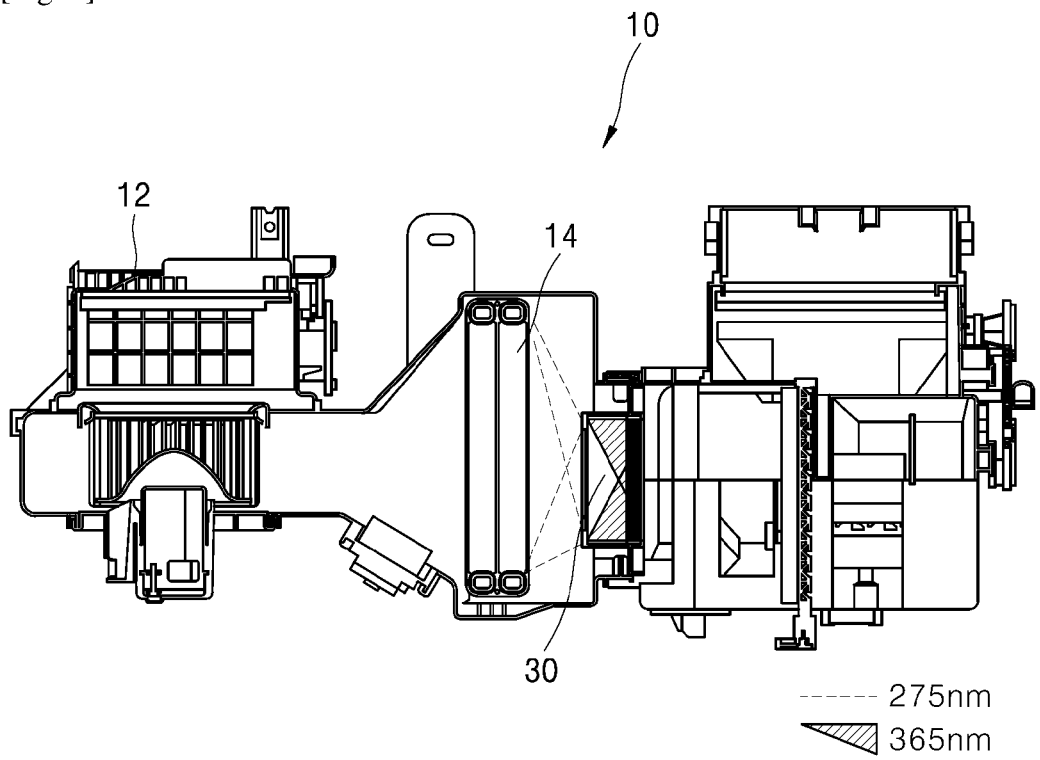

[Fig. 7]
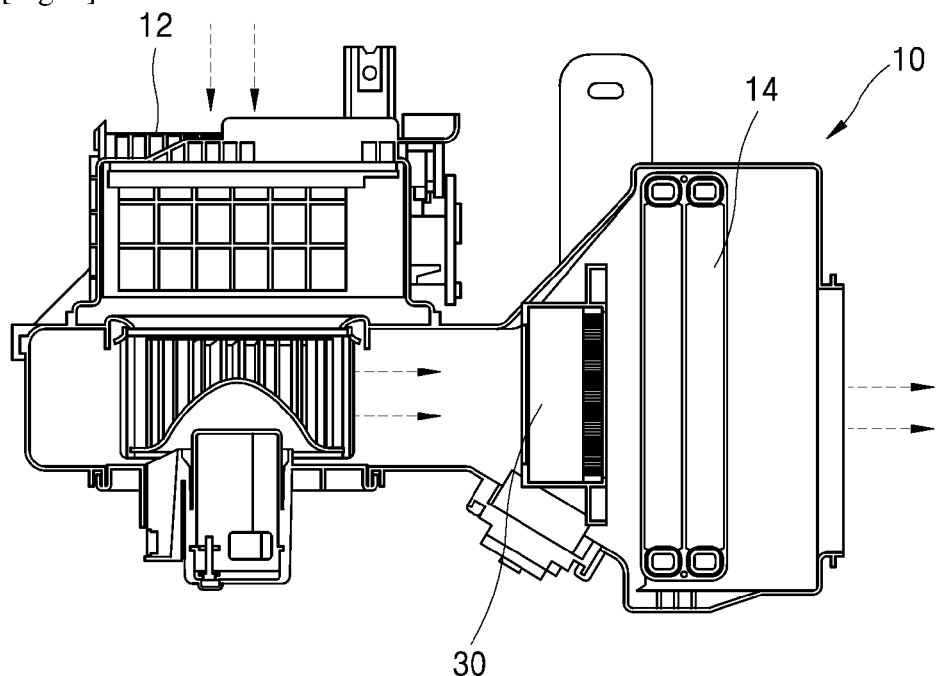
[Fig. 8]
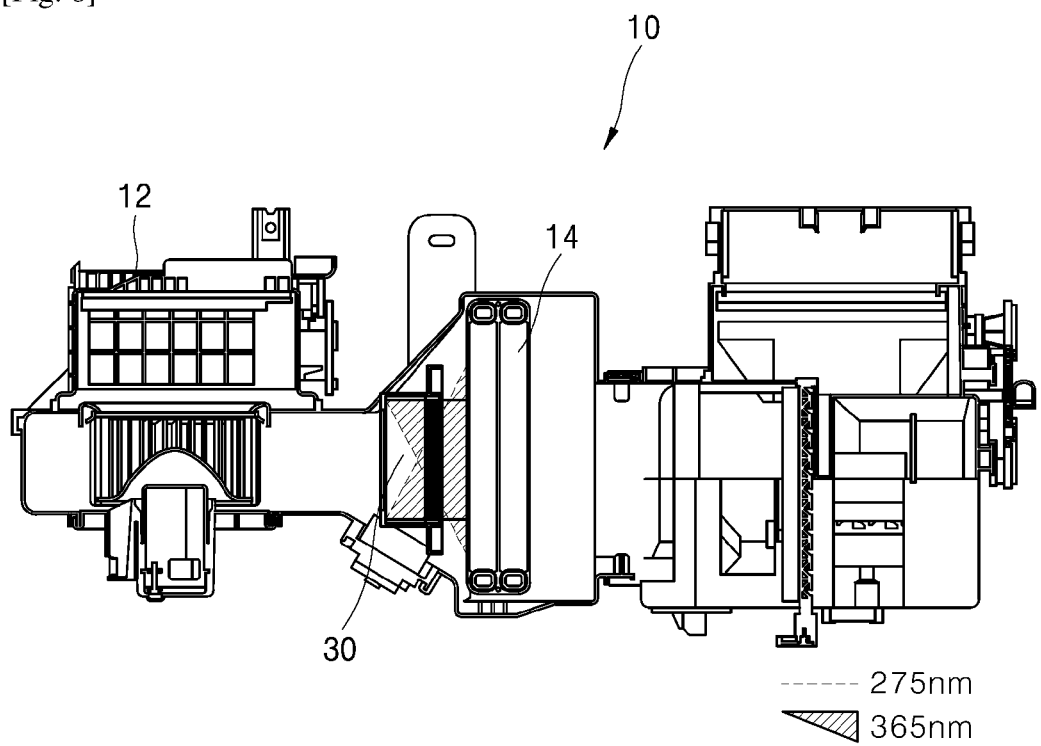

[Fig. 9]
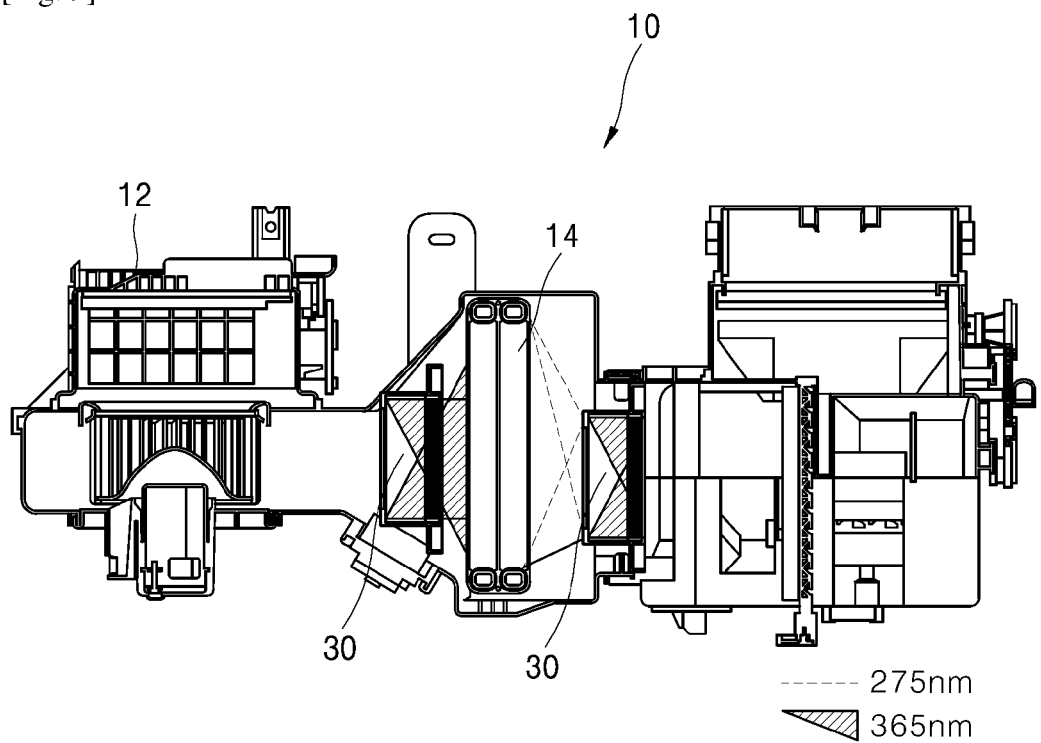
----- 275nm
▨ 365nm
[Fig. 10]
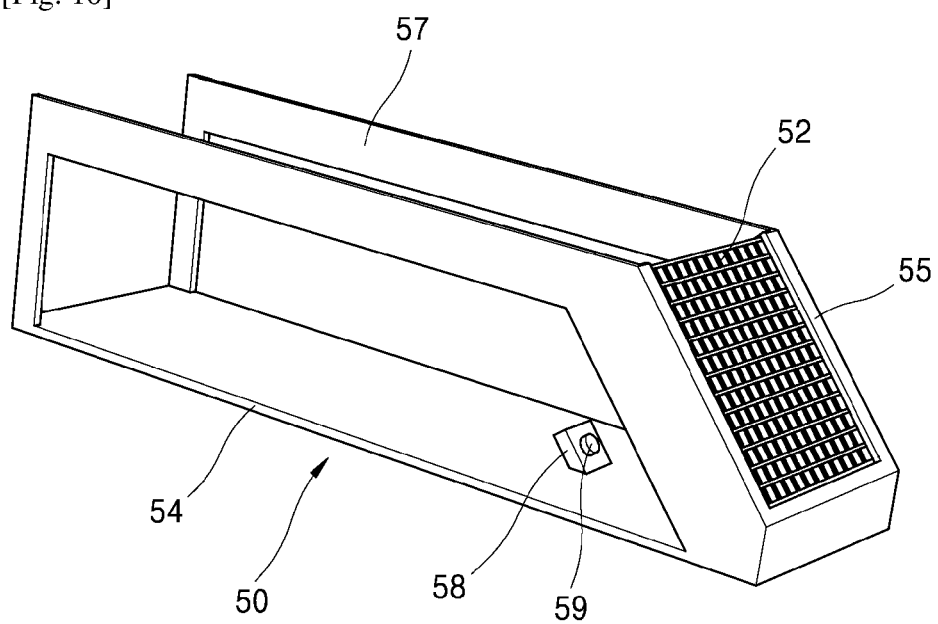

[Fig. 11]
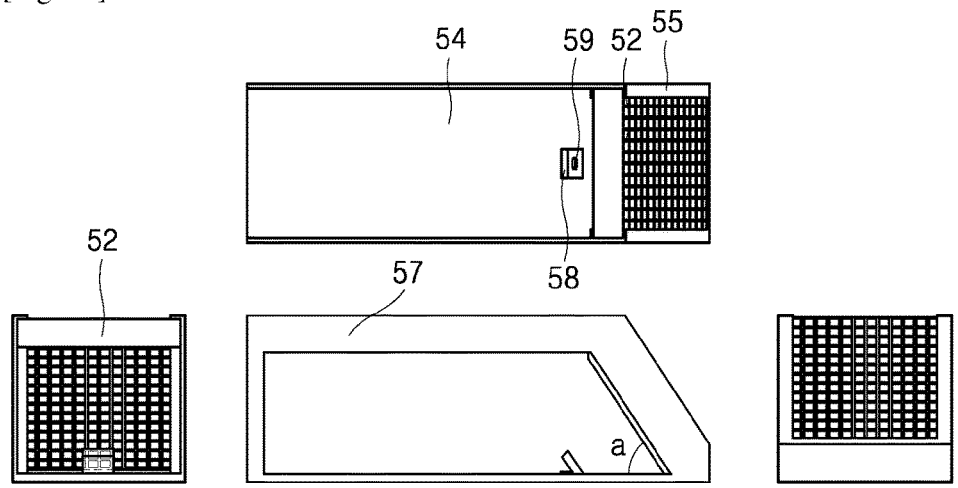
[Fig. 12]
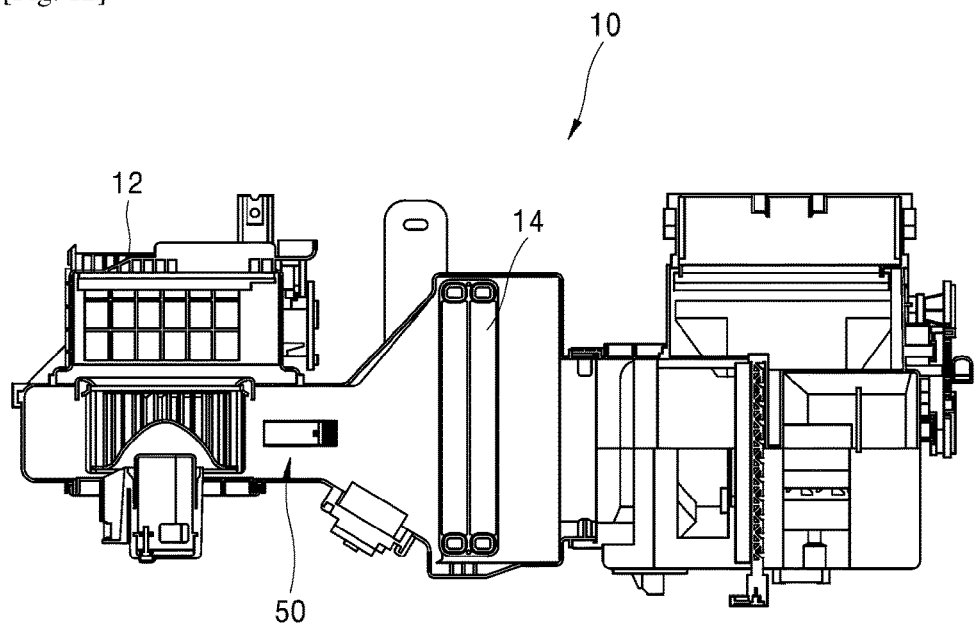
[Fig. 13]
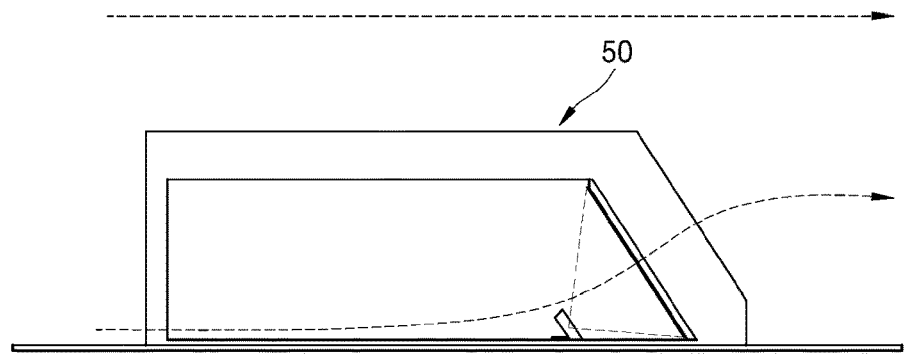

[Fig. 14]
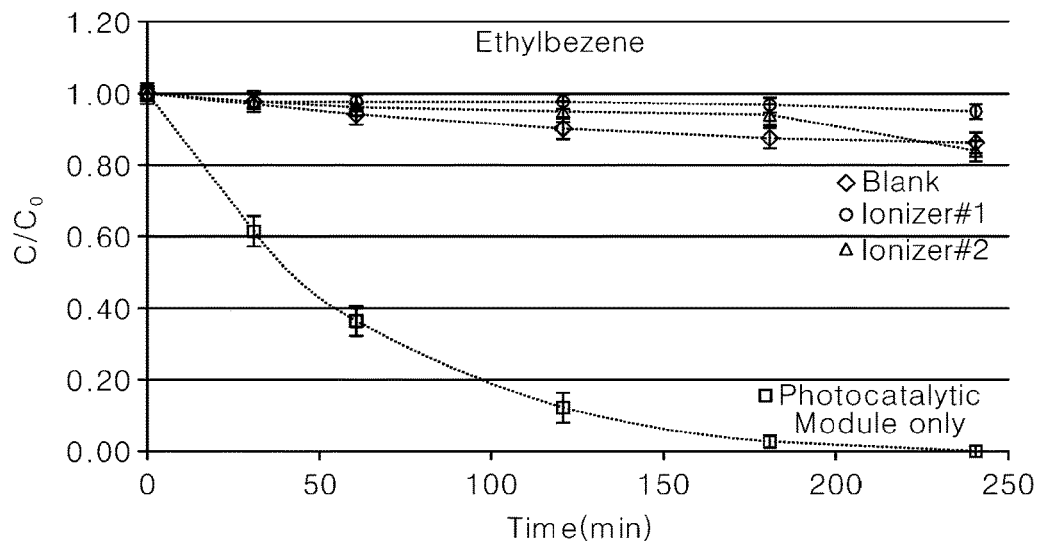
[Fig. 15]
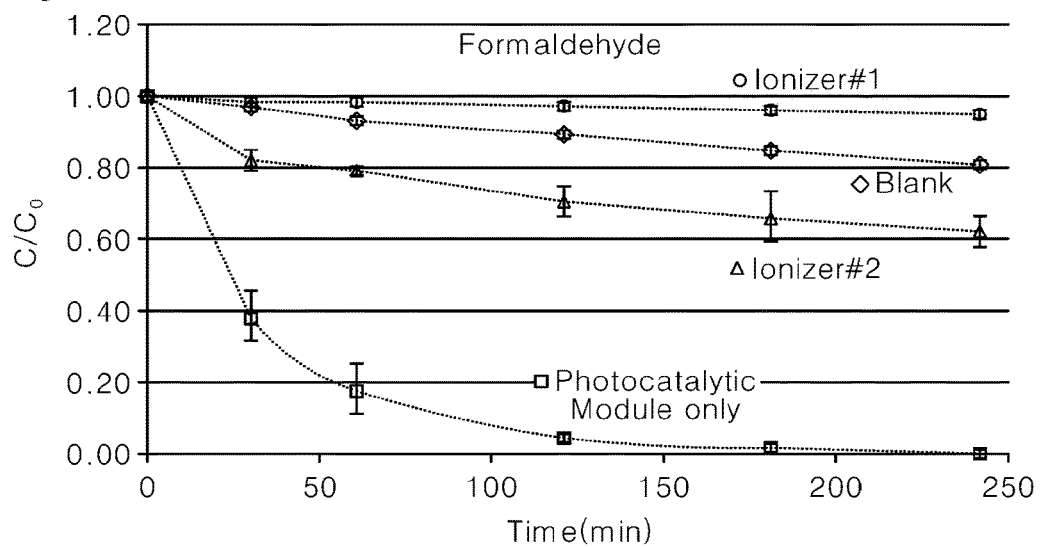
[Fig. 16]
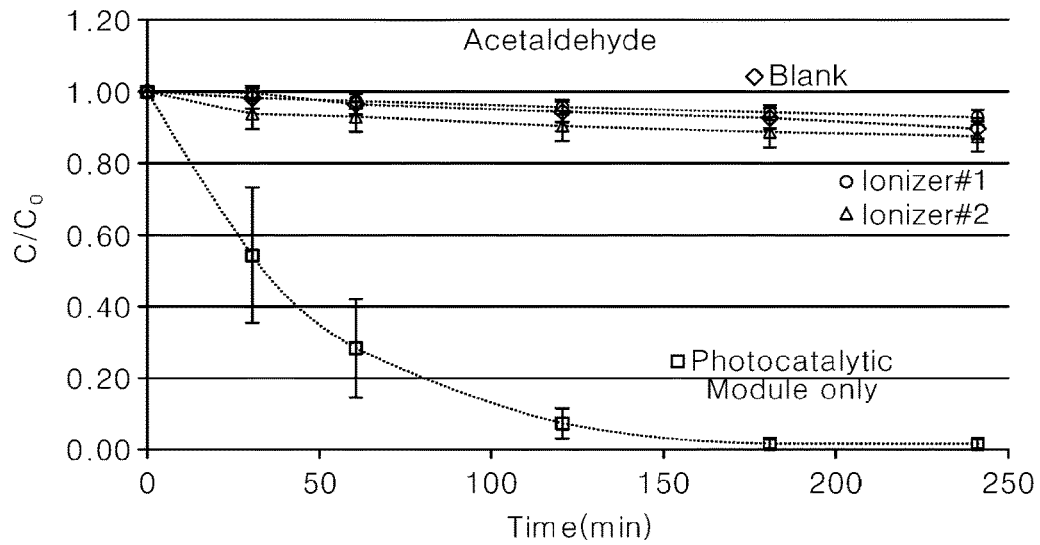

[Fig. 17]
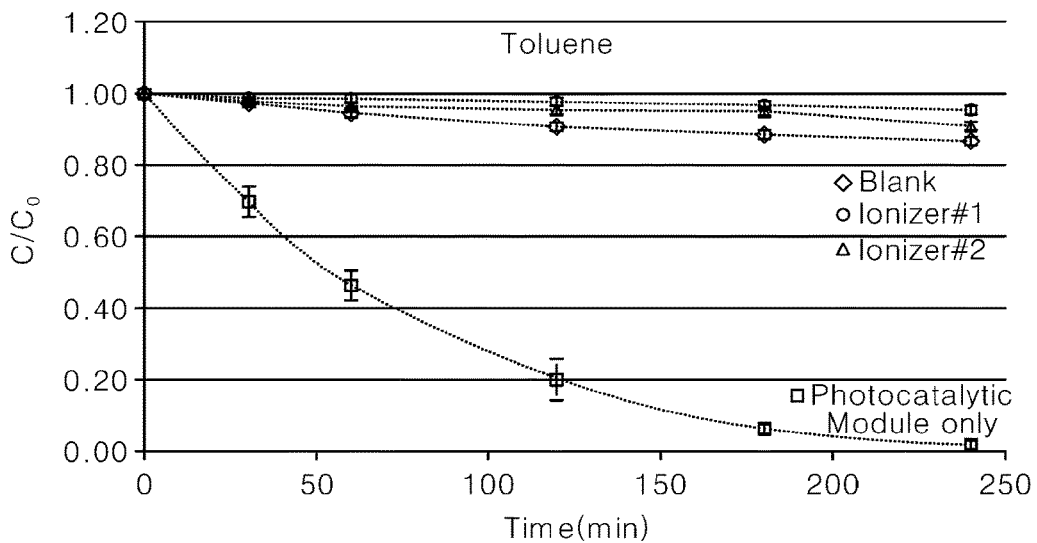
[Fig. 18]
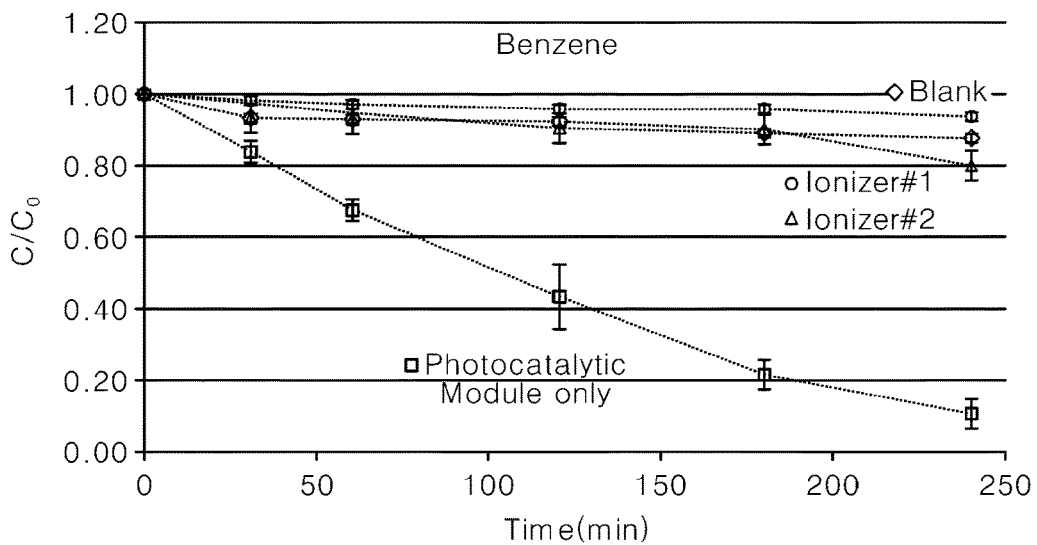
[Fig. 19]
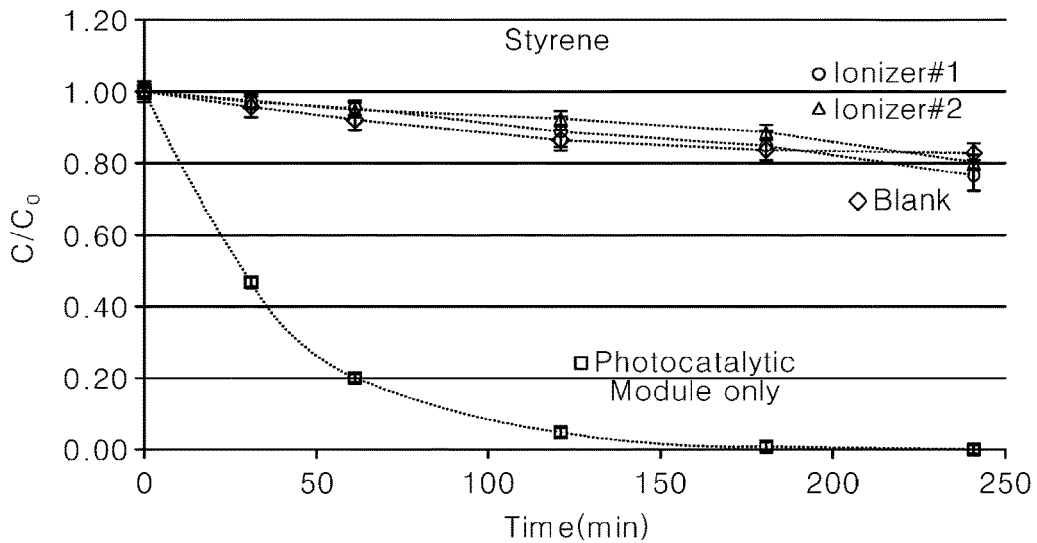

[Fig. 20]
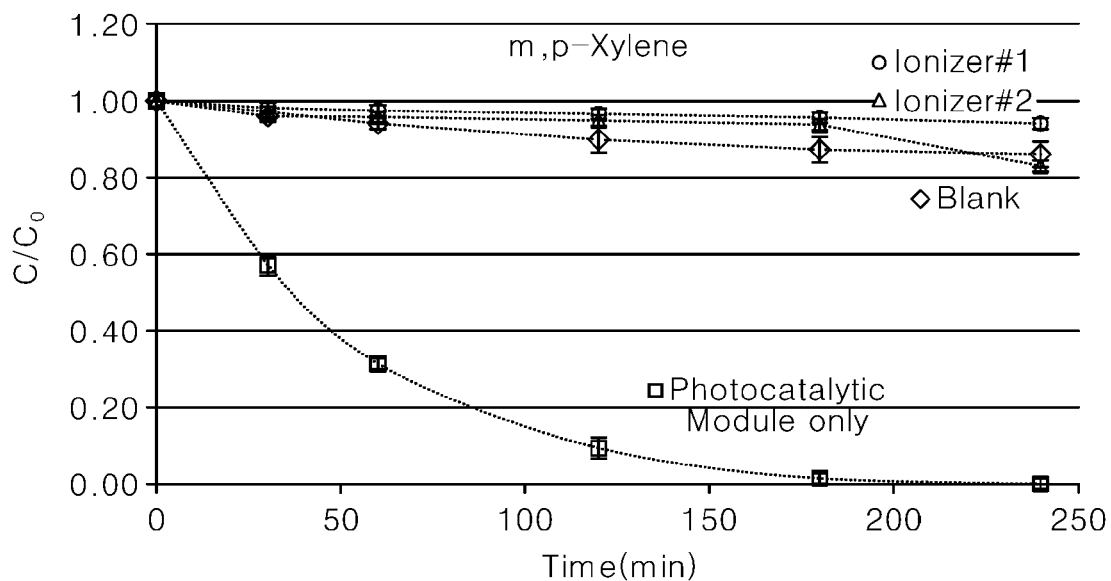
[Fig. 21]
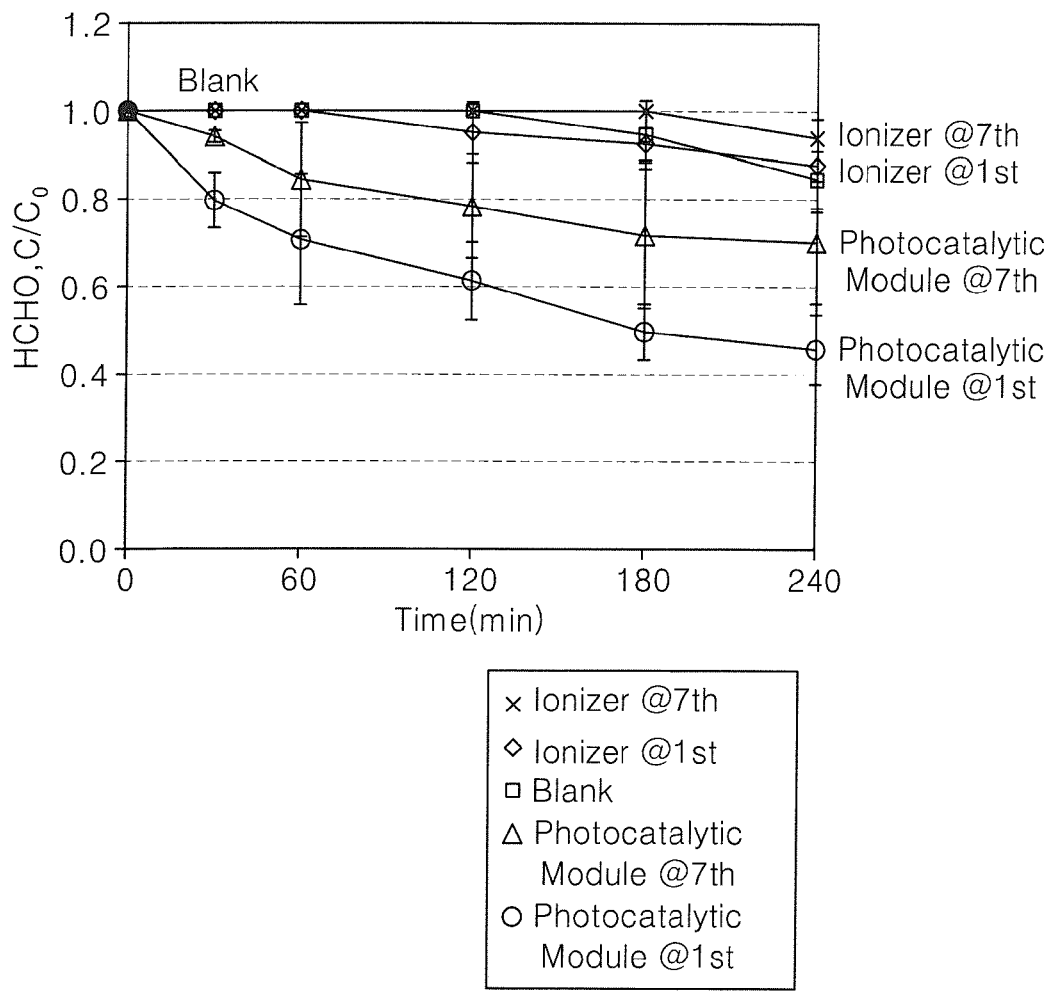

[Fig. 22]
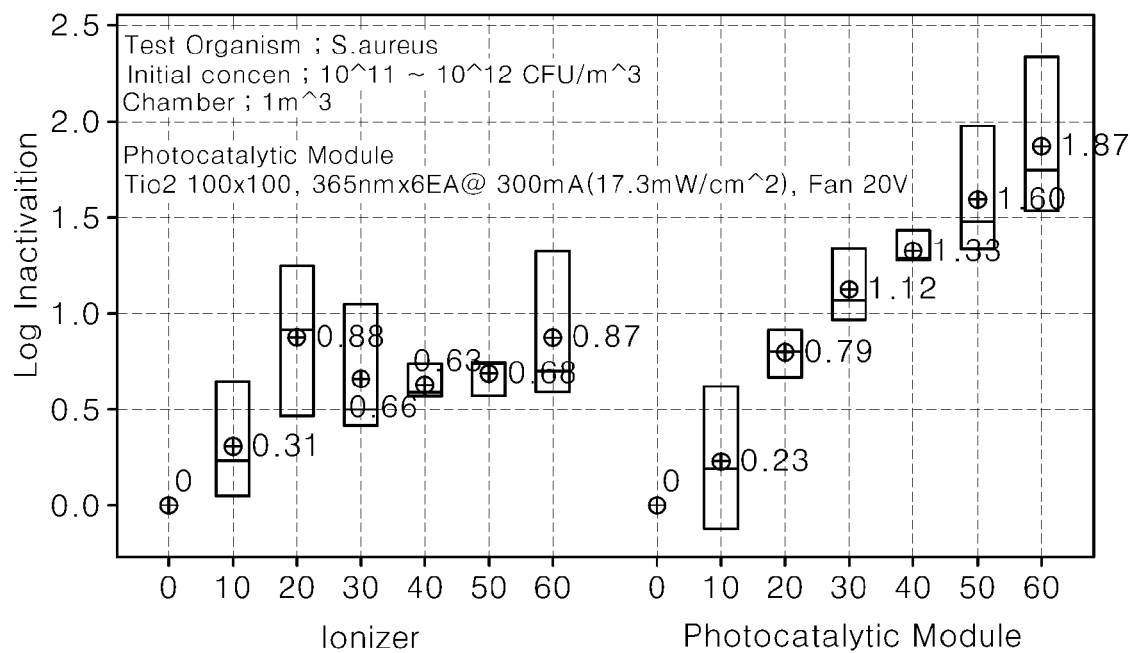

PHOTOCATALYTIC MODULE FOR AUTOMOBILE AIR CONDITIONER AND AUTOMOBILE AIR CONDITIONER HAVING THE SAME

CROSS REFERENCE TO RELATED APPLICATIONS

This patent document is a 35 U.S.C. § 371 National Stage application of PCT Application No. PCT/KR2015/013673, filed on Dec. 14, 2015, which further claims the benefits and priorities of prior Korean Patent Application No. 10-2014-0179706, filed on Dec. 12, 2014, and Korean Patent Application No. 10-2015-0093755, filed on Jun. 20, 2015. The entire disclosures of the above applications are incorporated by reference in their entirety as part of this document.

TECHNICAL FIELD

The present invention relates to a photocatalytic module for an automobile air conditioner and an automobile air conditioner having the same and, more particularly, to a photocatalytic module capable of eliminating various germs resulting from dew formed on an evaporator installed in an automobile air conditioner and corresponding bad smell, and an air conditioner having the same.

BACKGROUND ART

An automobile air conditioner is a device for adjusting temperature of the inner space of an automobile by forcibly circulating air staying in the inner space of the automobile through a duct and causing the air to be cooled by the evaporator installed in the duct and to be discharged into the internal space of the automobile.

The evaporator of the air conditioner remains cool due to latent heat absorbed by the refrigerant as the refrigerant is evaporated. In addition, when relatively warm air meets the evaporator, moisture in the air is condensed to water on the surface of the evaporator.

This mechanism may not cause a serious problem if the air conditioner is persistently operated. However, if operation of the air conditioner is stopped, circulation of air is stopped and condensed water remains on the surface of the evaporator. Thereby, various kinds of microbes and germs reproduce in the condensed water, causing bad smell.

The biggest problems in conditioning air using an air conditioner is that water remaining on the evaporator due to the temperature of the evaporator of the air conditioner lower than that of air causes reproduction of germs and mold around the evaporator and the reproduced germs and mold move around in the air in the indoor space as the evaporator forcibly circulating the air to increase the heat exchange efficiency. Germs and mold are direct harm to human bodies and the bad smell caused by reproduction of germs is very unpleasant.

For air conditioners for domestic use or use in a building, after air cooling through the refrigerant is stopped, air is forcibly circulated for a certain time in order to vaporize condensed water on the surface of the evaporator to prevent the aforementioned problems. On the other hand, in the case of automobile air-conditioners, once the automobile is thus switched off, such operation cannot be performed. As a result, condensed water remains on the evaporator for a long time, causing reproduction of germs and microbes.

To partially prevent this problem, drivers form a habit of stopping cooling the air around five minutes before stopping the engines and letting air flow after air cooling is stopped. However, it is difficult to correctly determine the time to stop the engine. In addition, humid air begins to make the driver unpleasant from the time five minutes before the driver gets off the automobile.

It is widely known that germs are the cause of bad smells. Conventionally, various technologies of sterilization through direct radiation of ultraviolet light onto the evaporator have been proposed to suppress reproduction of germs. Application of an ionizer or a photocatalytic filter has also been proposed.

However, since plates of the operator for heat exchange are arranged very close to each other, ultraviolet light cannot reach the air deep in the space between the plates. Accordingly, radiation of ultraviolet light alone is not sufficient to suppress reproduction of germs around the evaporator. As a result, germs reproducing on the evaporator produce bad smell as in the previous case, and thus radiation of ultraviolet light onto the evaporator cannot be a solution. Thereby, the emotional quality of the evaporator is lowered for users who are exposed to bad smell.

Korean Patent Application Publication No. 2015-25967 proposes a technology of utilization of photocatalytic reaction. In contrast with the disclosure of this document, the catalytic reaction occurs only on the surface of a photocatalytic material, and thus active radical cannot be separated from the photocatalytic material. Accordingly, photocatalytic reaction cannot directly destroy germs reproducing on the evaporator.

In addition, the sterilization or deodorization efficiency of the ionizer is lower than that of photocatalytic reaction. Further, as the ionizer is installed so as not to obstruct airflow, the efficiency of the ionizer is further lowered.

PRIOR ART LITERATURE

Patent Documents

Korean Patent Application Publication No. 2015-25967
Korean Patent Application Publication No. 2015-24011
Korean Patent Application Publication No. 2015-24012
Korean Patent Application Publication No. 2015-11141
Korean Patent Application Publication No. 1997-34679

DISCLOSURE

Technical Problem

It is an aspect of the present invention to provide a photocatalytic module for an automobile air conditioner which is capable of removing bad smell produced by reproduction of microbes in germs caused by condensed water formed on the evaporator of the automobile air conditioner, and an automobile air conditioner having the same.

Technical Solution

The present invention devised to solve the problem provides a structure for performing sterilization and removing hazardous gases by installing a photocatalytic module near an evaporator installed in the duct of an automobile air conditioner.

In accordance with one aspect of the present invention, a photocatalytic module 30 installed in an automobile air conditioner duct 10, the photocatalytic module including a duct fixation frame 34 coupled to an inner wall or a joint of the duct 10 to fix the module to fix the duct, a filter fixation frame 35 connected to the duct fixation frame to fix a photocatalytic filter 32, the photocatalytic filter 32 fixed by the filter fixation frame 35, the photocatalytic filter 32 being formed by applying a photocatalytic material onto a supporter having a shape of a plurality of cells neighboring each other and provided with a plurality of airflow paths, and a spacing member 36 connected to the duct fixation frame 34 and provided with a substrate 38 equipped with an ultraviolet (UV) light emitting diode (LED) 39 for radiating ultraviolet light toward the photocatalytic filter 32.

The duct fixation frame 34 is a circular shape corresponding to a cross-section shape of the duct 10, wherein the photocatalytic filter 32 is formed to fill an interior of a circular part of the duct fixation frame 34.

The photocatalytic filter is fixed to the filter fixation frame 35 while being fitted into the interior of the circular part of the duct fixation frame 34.

The circular part of the duct fixation frame 34 is a solid shape.

The spacing member 36 is provided with a circular substrate installation surface extending from an inner diameter portion of the circular part of the duct fixation frame 34 in a direction substantially identical to a flow direction of air, wherein the substrate 38 is installed on the substrate installation surface.

The LED 39 for radiating ultraviolet light having a peak wavelength between 340 nm and 380 nm toward the photocatalytic filter is installed in the substrate 38 installed on the substrate installation surface.

A UV LED for radiating ultraviolet light having a peak wavelength between 260 nm and 280 nm is further installed on the substrate 38 installed on the substrate installation surface.

The ultraviolet light having the peak wavelength between 260 nm and 280 nm is radiated in a direction opposite to an installation direction of the photocatalytic filter.

In accordance with another aspect of the present invention, a photocatalytic module 50 installed at an automobile air conditioner duct 10, including a duct fixation frame 54 adjacent to an inner wall of the duct 10, a filter fixation frame 55 having one end connected to the duct fixation frame, the filter fixation frame 55 fixing the photocatalytic filter 52, a photocatalytic filter 52 fixed by the fixation frame 55, being formed by applying a photocatalytic material onto a supporter having a shape of a plurality of cells neighboring each other and provided with a plurality of airflow paths, and a substrate 58 fixed to the duct fixation frame 54 and equipped with an ultraviolet (UV) light emitting diode (LED) 59 for radiating ultraviolet light toward the photocatalytic filter 52.

The photocatalytic module further includes a reinforcement frame 57 for connecting the other end of the filter fixation frame 55 to the duct fixation frame 54 and reinforcing a rigidity of the filter fixation frame 55.

The photocatalytic filter is fixed to form an acute angle with the duct fixation frame 54.

The acute angle is between 40° and 85°.

The UV LED 59 radiates ultraviolet light having a peak wavelength between 340 nm and 380 nm toward the photocatalytic filter.

A UV LED for radiating ultraviolet light having a peak wavelength between 260 nm and 280 nm is further installed on the substrate 38.

In accordance with another aspect of the present invention, an automobile air conditioner having the photocatalytic module according to any one of claims 1 to 13 installed therein, wherein the LED is disposed upstream of the photocatalytic filter on a flow path of the duct.

The photocatalytic module is installed upstream of an evaporator on the flow path of the duct, and ultraviolet light radiated from the photocatalytic module is directed toward the evaporator.

Advantageous Effects

According to embodiments of the present invention, bad smell produced on the evaporator installed in an automobile air conditioner is prevented from entering the indoor space of an automobile, and germs and microbes reproducing on the evaporator may be prevented from floating in the air and threatening health of persons in the automobile.

In addition, the photocatalytic module of the present invention lessens a burden of maintenance as it does not need to be separately replaced or exchanged until the service life of the automobile ends.

In addition, the photocatalytic module of the present invention is very convenient to use as it can be easily installed without changing the structure of the air conditioner of the automobile.

In addition, photocatalytic reaction efficiency may be enhanced while resistance to airflow around the air conditioner of the automobile is minimized. Accordingly, the photocatalytic module is particularly suitable for an installation space in a compact automobile air conditioner.

Further, the photocatalytic module of the present invention is capable of decomposing volatile organic compounds and radiating ultraviolet light directly onto the evaporator. Accordingly, direct sterilization of the evaporator may also be expected from the photocatalytic module.

Effects of the present invention are not limited to those described above and other effects of the present invention will be apparent to those skilled in the art from the following descriptions.

DESCRIPTION OF DRAWINGS

FIG. 1 is a perspective view illustrating installation of a photocatalytic module of the present invention in an automobile air conditioner.

FIG. 2 shows a perspective view and a cross-sectional perspective view illustrating the photocatalytic module of FIG. 1.

FIG. 3 is a lateral cross-sectional view illustrating an automobile air conditioner having the photocatalytic module of FIG. 1 installed therein.

FIG. 4 is a lateral cross-sectional view illustrating the whole system of automobile air conditioner having the photocatalytic module of FIG. 1 installed therein.

FIGS. 5 and 6 are lateral cross-sectional views illustrating radiation of ultraviolet light from an LED of the photocatalytic module of FIG. 4, and FIG. 7 is a lateral cross sectional view illustrating an automobile air conditioner having the photocatalytic module installed therein according to another embodiment.

FIG. 8 is a lateral cross section view illustrating the whole system of the automobile air conditioner shown in FIG. 7.

FIG. 9 is a lateral cross section view illustrating the whole system of an automobile air conditioner having the photocatalytic modules of FIGS. 6 and 8 installed therein.

FIG. 10 is a perspective view illustrating a photocatalytic module according to another embodiment of the present invention.

FIG. 11 is an orthographic view illustrating the photocatalytic filter of FIG. 10.

FIG. 12 is a cross-sectional view illustrating installation of the photocatalytic module of FIG. 10 in an automobile air conditioner.

FIG. 13 is a cross-sectional view illustrating flow of air through a photocatalytic module installed in a duct.

FIGS. 14 to 21 are graphs depicting results of experiments comparing performance of the photocatalytic module of the present invention with reference of a conventional ionizer in terms of hazardous gas decomposition.

FIG. 22 is a graph depicting the result of an experiment comparing performance the photocatalytic module of the present invention with that of a conventional ionizer in terms of sterilization.

BEST MODE

Hereinafter, embodiments of the present invention will be described in detail with reference to the accompanying drawings.

The present invention is not limited to exemplary embodiments disclosed herein but may be implemented in various different forms. The exemplary embodiments are provided for making the disclosure of the present invention thorough and for fully conveying the scope of the present invention to those skilled in the art. Constituents of a one embodiment may be combined with constituents of another embodiment, which is also within the scope of the present invention.

Embodiment 1

FIG. 1 is a perspective view illustrating installation of a photocatalytic module of the present invention in an automobile air conditioner. FIG. 2 shows a perspective view and a cross-sectional perspective view illustrating the photocatalytic module of FIG. 1. FIG. 3 is a lateral cross-sectional view illustrating an automobile air conditioner having the photocatalytic module of FIG. 1 installed therein. FIG. 4 is a lateral cross-sectional view illustrating the whole system of an automobile air conditioner having the photocatalytic module of FIG. 1 installed therein.

Referring to FIG. 1, a photocatalytic module 30 according to the present invention is installed in an automobile air conditioner. Specifically, the photocatalytic module 30 is installed in a duct 10, which is an airflow path in the air conditioner. The duct 10 is provided with an air inlet 12 for suctioning air in the automobile. The air suctioned through the air inlet 12 is pressurized and caused to flow in the duct by a fan in the duct.

Referring to FIGS. 3 and 4, air is introduced through the air inlet 12 and pressurized by the fan to flow along the duct. The flowing air is cooled in an expanded space while passing through an evaporator 14, and then discharged from the duct. According to one embodiment of the present invention, as shown in the figure, air passing through the evaporator is caused to pass through the photocatalytic module 30 and then be discharged into the indoor space of the automobile. Specifically, flowing air passing through the evaporator may be introduced into the indoor space of the automobile along with various microbes and germs, which are reproduced by condensed water on the evaporator, and bad smell and hazardous gas produced by the microbes and germs. According to an embodiment of the present invention, the photocatalytic module is installed in the downstream of airflow of the evaporator providing a cause of the aforementioned issue such that air contaminated while passing through the evaporator is purified by the photocatalytic module.

Referring to FIG. 2, the photocatalytic module includes a photocatalytic filter 32 and an LED 39 for radiating ultraviolet light onto the photocatalytic filter. The photocatalytic filter 32 and the LED 39 are installed in a housing formed of a synthetic resin. The housing is not necessarily formed of a synthetic resin. However, the housing is preferably fabricated using a synthetic resin which is lightweight and inexpensive.

The photocatalytic filter 32 is installed at the center of the housing, and a duct fixation frame 34 to engage with in the inner wall of the duct 10 to fix the photocatalytic module 30 is formed on the circumference of the housing. That is, the inner circumferential surface of the duct fixation frame 34 faces the outer circumferential surface of the photocatalytic filter 32, and the outer circumferential surface of the duct fixation frame 34 faces the inner circumferential surface of the duct 10. The duct fixation frame 34 is not provided with any hole therein. Accordingly, air flowing in the duct essentially passes through the photocatalytic filter 32.

The photocatalytic filter 32 is fixed to the housing by a filter fixation frame 35 while being accommodated in the inner circumferential surface of the duct fixation frame 34. Various well-known techniques may be used to fix the photocatalytic filter 32 to the housing, and a gap between the photocatalytic filter and the housing only needs to be sealed to an extent by which the air flowing in the duct from is prevented from bypassing the photocatalytic filter.

As shown in FIG. 2, the photocatalytic filter 32 has a honeycomb structure in which a plurality of cells having a square cross section and neighboring each other as airflow paths. However, the cross-sectional shape of the cell is not limited to the square shape. Cells having the same shape such as a regular hexagon may neighbor each other to prevent creation of a gap.

The photocatalytic filter 32 may have a size corresponding to the cross-sectional area of the duct. Since the diameter or cross-section area of a duct used for automobile air conditioners does not vary significantly among automobiles, the photocatalytic filter 32 may have a constant size. According to the embodiment of the present invention, the photocatalytic filter 32 has the shape of a square each side of which is about 10 cm with a thickness of about 10 mm (strictly speaking, a hexahedron which is small in height and has a square-shaped bottom). The photocatalytic filter 32 is applicable to various automobiles by adjusting the size of the outer circumference of the duct fixation frame 34 of the housing.

Meanwhile, as shown in FIG. 2, the housing is provided with a spacing member 36 extending in the same direction as the flow direction of air. A substrate 38 provided with the LED 39 is installed at one end of the space member 36. The number and installation positions of the LEDs can be properly adjusted according to the size of the photocatalytic filter. Preferably, as the photocatalytic filter 32 having the shape of a square with a length of 10 cm on each side is installed, four LEDs having a dispersion angle of 120° are installed at a position spaced by 2 to 3 cm from the photocatalytic filter such that ultraviolet light is uniformly radiated onto the photocatalytic filter by the respective LEDs.

While FIG. 2 illustrates the spacing member as being a solid plate, embodiments of the present invention are not limited thereto. The spacing member may have any shape as long as it can stably fix the substrate at a position spaced from the photocatalytic filter.

The ultraviolet light absorption rate of the photocatalytic filter which is coated with $TiO_2$ nano-powder thereon becomes highest when the ultraviolet light wavelength is around 270 nm, and linearly decreases as the wavelength increases to 400 nm. Accordingly, it may appear that using an LED having 270 nm as the peak wavelength is favorable. However, when the LEDs are used actually, it can be found that best photocatalytic activation is obtained with an LED with 365 nm as the peak wavelength. This is because of light emission efficiency of the LED. That is, as the peak wavelength decreases, the amount of light emitted from an LED decreases drastically. Accordingly, best photocatalytic reaction can be obtained with an LED having a peak wavelength equal to 365 nm actually.

In other words, for an LED having a peak wavelength around 270 nm, intensity of emitted ultraviolet light is very low compared to a proper intensity of ultraviolet light required on the surface of the photocatalytic filter, and thus photocatalytic reaction is not active. If the number of the LEDs is increased to increase the intensity of ultraviolet light in consideration of this fact, this may increase the size of the substrate and interrupts flow of air. Further, increasing the number of LEDs is not preferable since it drastically increases manufacturing costs and power consumption.

It was found in an experiment that deodorization efficiency of the photocatalytic filter is remarkably lowered when an LED having a peak wavelength less than or equal to 340 nm is used.

In addition, if an LED having a peak wavelength greater than or equal to 380 nm is used, the ultraviolet light absorption rate of photocatalytic reaction is significantly lowered to an extent that there is no difference from that of a conventional ultraviolet lamp such as black light and thus use of the LED is not meaningful.

The results of the experiment show that the highest deodorization performance of the photocatalytic filter can be obtained when an LED having a peak wavelength between 360 nm and 370 nm is used. However, it should be understood that the scope of the present invention is not limited to the aforementioned peak wavelength range.

As described above, the photocatalytic filter has a structure in which a photocatalytic material is applied onto a supporter constructed by a plurality of cells forming an airflow path having a hexagon-shaped or square-shaped cross section similar to a honeycomb shape. The inlet of the airflow path is disposed in the flow direction of air or disposed to face an ultraviolet light source. With the photocatalytic filter having this form, ultraviolet light can be emitted not only onto the outer surface of the photocatalytic filter on to the inner surface of the airflow path. Thereby, photocatalytic reaction may be boosted.

The distance between the LED 39 and the front face of the photocatalytic filter 40 facing the same depends on the area and intensity of ultraviolet light reaching the photocatalytic material according to the distance between the LED substrate and the photocatalytic filter. It can be seen from the results of the experiment that deodorization efficiency greatly decreases when the distance between the LED and the front face of the photocatalytic filter decreases below 2 cm or increase beyond 4 cm.

If the distance between the LED and the front face of the photocatalytic filter decrease below 2 cm, the area of the photocatalytic filter onto which ultraviolet light is emitted decreases, while intensity of ultraviolet light per unit area of the catalytic filter excessively increases such that photocatalytic activation efficiency does not increase anymore and saturated. If the distance between the LED and the front face of the photocatalytic filter increases beyond 4 cm, intensity of ultraviolet light per unit area of the photocatalytic filter decreases, and thus the degree of photocatalytic activation is lowered.

It is needed to consider the intensity of ultraviolet light reaching the photocatalytic filter. It may be thought that high intensity of ultraviolet light reaching the surface of the photocatalytic filter will increase the photocatalytic reaction efficiency. However, the experiment shows that the photocatalytic reaction efficiency increases along with intensity of ultraviolet light to a certain level, and then does not increase anymore even if the intensity is further increased. It can be seen from the result of the experiment that increasing the ultraviolet light intensity beyond about 18 mW/cm$^2$ significantly slows trend of increase of the photocatalytic reaction efficiency when an LED having a peak wavelength between 360 nm and 370 nm is used. In addition, if the intensity of ultraviolet light is less than about 12 mW/cm$^2$, the intensity of ultraviolet light is insufficient and thus the photocatalytic reaction efficiency is greatly lowered.

Meanwhile, the flow direction of air also needs to be considered. In this embodiment, the flow direction of air is identical to the direction in which the LED serving as the ultraviolet light source faces the photocatalytic filter.

This arrangement is based on the result of an experiment. It has been found from the experiment that driving air to flow in the same direction as the direction in which the ultraviolet light source faces the photocatalytic filter exhibits much higher purification efficiency than driving the air to flow in the opposite direction.

Since the photocatalytic filter has a structure of multiple airflow paths through which air must flow, air pressure is lowered due to flow resistance as air passes through the photocatalytic filter. Meanwhile, photocatalytic reaction is promoted as the surface of the photocatalytic material contacts as much air as possible. Accordingly, higher decomposition efficiency of a hazardous gas in the air can be obtained when air contacts the photocatalytic material before pressure drop occurs in the air through the photocatalytic filter than when the air contacts the photocatalytic material after pressure of the air drops through the photocatalytic filter. Accordingly, in this embodiment, the air is allowed to flow in the direction in which the ultraviolet light source faces the photocatalytic filter, such that the air purification efficiency of the photocatalytic filter is further enhanced.

In installing the photocatalytic module 30, the duct fixation frame 34 of the photocatalytic module is preferably installed at the connection portion of the duct as shown in FIGS. 1 and 4. When the photocatalytic module 30 is installed in the duct which is detached as shown in FIG. 1 and then the duct is connected as shown in FIG. 4, the photocatalytic module according to the present invention may be easily installed in the conventional duct structure.

According to the first embodiment, photocatalytic reaction may be caused by radiation of ultraviolet light whose peak wavelength is 365 nm onto the photocatalytic filter 32 as shown in FIG. 5.

Embodiment 2

As a variant of the first embodiment, it may be possible to provide both an LED for activation of photocatalytic reaction and an LED producing a wavelength for sterilization. For example, in the first embodiment illustrated in FIGS. 1 to 4, LEDs for radiating ultraviolet light having a peak wavelength exhibiting high sterilization efficiency according to direct radiation may be installed on the other surface of the substrate 38 installed on the photocatalytic module 30, namely on the opposite surface to the surface on which the LED 39 radiating ultraviolet light onto the photocatalytic filter 32 is installed, such that the LEDs radiate ultraviolet light for sterilization onto the evaporator 14. Thereby, the evaporator may be directly sterilized as shown in FIG. 6.

Regarding peak wavelengths exhibiting high sterilization efficiency, it has been conventionally known that a wavelength around 253 nm exhibits the highest sterilization efficiency. However, it has been found in the experiment that a wavelength around 270 nm rather exhibits higher sterilization efficiency. This is because germs in the scale of microorganism produced due to water formed on the evaporator have the highest ultraviolet light absorption rate of DNA at around the wavelength of 270 nm, in contrast with typical cells. By providing a UV LED capable of adjusting the peak wavelength in contrast with the conventional ultraviolet lamp and setting the UV LED to a peak wavelength producing the highest adoption rate, sterilization efficiency may be further enhanced. Accordingly, the sterilization UV LED adopted in the present invention may use ultraviolet light having a peak wavelength within the range you pitching about 260 nm and about 280 nm Embodiment 3

FIG. 7 is a lateral cross sectional view illustrating an automobile air conditioner having the photocatalytic module installed therein according to another embodiment, and FIG. 8 is a lateral cross section view illustrating the whole system of the automobile air conditioner shown in FIG. 7.

In describing another embodiment below, description of elements which are already described in the first embodiment will not be given. Accordingly, it is apparent that details described in the first embodiment but not in this embodiment may also be applied if they are not against technical features of this embodiment. This rule may be applied to all embodiments. In the third embodiment illustrated in FIGS. 7 and 8, the photocatalytic module 30 is installed at a different position.

If the photocatalytic module 30 is positioned at the front part of the evaporator 14 as shown in the figure, ultraviolet light emitted from the photocatalytic module 30 is radiated onto the evaporator 14 by passing through the photocatalytic filter 32. Thereby, the surface of the evaporator may be directly sterilized by ultraviolet light.

For example, if LEDs 39 for radiating ultraviolet light having a peak wavelength around about 270 nm, e.g., a peak wavelength of 275 nm are installed on the substrate 38 of the photocatalytic module 30, or if a UV LED producing a peak wavelength of 365 nm for a photocatalytic direction and a UV LED producing a peak wavelength of 275 nm for direct sterilization are installed on the substrate together, the sterilization effect according to direct radiation of ultraviolet light may be more securely obtained as shown in FIG. 8.

Embodiment 4

It is also possible to install photocatalytic modules 30 both downstream of the evaporator 14 as shown in FIG. 3 and upstream of the evaporator 14 as shown in FIG. 7. In this case, the photocatalytic modules 30 proposed in the first embodiment may not be installed only, but also the photocatalytic module having the form according to the third embodiment may be installed upstream of the evaporator and the photocatalytic module having the form according to the second embodiment may be installed downstream of the evaporator, as shown in FIG. 9.

In addition to the examples as described above, other variants having various forms and combinations are also possible.

According to the configuration of the photocatalytic filter and the UV LED for activating the same, when germs or microbes entering the air around the evaporator pass through the photocatalytic modules along with flowing air, they are destroyed by radicals activated by ultraviolet light and the photocatalytic material.

If ultraviolet light is directly radiated onto the evaporator as in the second and fourth embodiments, it is possible to suppress reproduction of germs and microbes in condensed water formed on the evaporator.

Embodiment 5

FIG. 10 is a perspective view illustrating a photocatalytic module according to another embodiment of the present invention, and FIG. 11 is an orthographic view illustrating the photocatalytic filter of FIG. 10. FIG. 12 is a cross-sectional view illustrating installation of the photocatalytic module of FIG. 10 in an automobile air conditioner, and FIG. 13 is a cross-sectional view illustrating flow of air through a photocatalytic module installed in a duct.

Referring to FIG. 10, as another embodiment of the present invention, a photocatalytic module 50 includes a photocatalytic filter 52 and a substrate 58, which are installed in a housing formed of a synthetic resin. An LED 59 for radiating ultraviolet light toward the photocatalytic filter 52 is installed on the substrate 58. Plural LEDs also can be installed on the substrate 58.

A duct fixation frame 54 forming the lower surface of the housing has a flat plate shape, contacts the automobile air conditioner duct 10, and serves to fix the photocatalytic module 50 to the duct 10. One end of the duct fixation frame 54 of the housing is provided with a filter fixation frame 55 inclined at a predetermined angle a with respect to the duct fixation frame 54 of the housing. The angle a formed between the filter fixation frame 55 and the duct fixation frame 54 is an acute angle. More specifically, the angle is determined within a range between about 40° and 85°. The photocatalytic filter 52, which has a honeycomb structure having a plurality of cells neighboring each other as airflow paths having a square-shaped cross section, is installed in the filter fixation frame 55. The substrate 58 may be fixed to the filter fixation frame 55 to form the same angle as the insulation angle of the photocatalytic filter 52.

The distance between the filter 52 and the LED 59 is about 2-3 cm.

The other upper end of the filter fixation frame 55 is connected to the other side of the duct fixation frame 54 by a reinforcement frame 57. The duct fixation frame 54 is formed to securely support the filter fixation frame 55 without obstructing air flow.

According to the fifth embodiment, the photocatalytic module 50 may be installed on a sidewall of the duct 10 such that the photocatalytic module closes only a part of the cross-section area of the duct 10, as shown in FIGS. 12 and 13, in contrast with the first to fourth embodiments. Installing only a part of the photocatalytic module 50 on the side surface of the duct may further reduce the number of parts of the conventional automobile air conditioner which should be altered, compared to the case where the photocatalytic module is installed in the joint of the duct. In addition, as the photocatalytic module 50 occupies only a part of the cross-section area of the duct for airflow, it rarely affects flow of air.

However, if the photocatalytic module 50 is installed at only a part of the cross-sectional area for airflow, flow resistance to the position where the photocatalytic module 50 is installed relatively increases, and accordingly air flowing in the duct may bypass the photocatalytic filter 52 and move along a path around the photocatalytic filter.

According to this embodiment, in consideration that air caused to flow in the duct in the longitudinal direction of the duct cannot reversely move, the filter fixation frame 55 is arranged to form an acute angle with respect to the duct fixation frame 54 such that air reaching a position at right front of the photocatalytic filter 52 passes through the photocatalytic filter rather than bypassing the photocatalytic filter. Thereby, sufficiently high photocatalytic reaction efficiency may be secured.

Compared to the first to fourth embodiments, the photocatalytic filter 52 may have the shape of a square each side of which is about 3.3 cm.

Experiment 1

FIGS. 14 to 20 are graphs depicting results of experiments comparing performance of the photocatalytic module of the present invention with that of a conventional ionizer in terms of hazardous gas decomposition.

In the experiment, a hazardous gas of 0.5 ppm was mixed with the air in the space of about 1 m$^3$, and the amount of hazardous gas concentration reduced over time was checked by operating a photocatalytic filter module of the present invention. As a control group, a commercially available ionizer was used to check the reduced amount of the hazardous gas in the same environment. The ionizer, which has dimensions of about 150 mm×150 mm×30 mm, is slightly bigger than the photocatalytic module of the present invention.

As a result of the experiments, the photocatalytic module of the present invention exhibited remarkably higher performance than the ionizer in decomposing or removing bad smell-causing hazardous gases such as formaldehyde, acetaldehyde, toluene, ethylbenzene, benzene, styrene, and xylene.

In addition, when the ozone emission rates in the experiment chambers were checked, ozone was not produced in the chamber where the photocatalytic module operated.

Experiment 2

FIG. 21 is a graph depicting a result of an experiment comparing performance of the photocatalytic module of the present invention with that of a conventional ionizer in terms of hazardous gas decomposition.

In the experiment, formaldehyde of 3±1 ppm was mixed with the air in the space of about 4 m$^3$, in which the temperature was 25±8° C. and the humidity was 55±15 RH %, and the amount of the hazardous gas concentration reduced over time was checked with the photocatalytic filter module of the fifth embodiment operating. The peak wavelength of ultraviolet light radiated from the LED was 365 nm, and the intensity of ultraviolet light measured on the surface of the photocatalytic filter was about 20.5 mW/cm$^2$. The flow rate of air caused to flow in the duct was changed from 2.9 CMM corresponding to a low running speed (1st speed) of the fan to 7.5 CMM corresponding to a high running speed (7th speed). As a control group, a commercially available ionizer was used to check the reduced amount of the hazardous gas in the same environment. The ionizer, which has dimensions of about 150 mm×150 mm×30 mm, is slightly bigger than the photocatalytic module of the present invention.

As a result of the experiment, the photocatalytic module of the present invention exhibited remarkably higher performance than the ionizer in decomposing or removing the hazardous gas, and this trend was uniform regardless of the flow rate of air in the duct.

Experiment 3

FIG. 22 is a graph depicting the result of an experiment comparing performance the photocatalytic module of the present invention with that of a conventional ionizer in terms of sterilization.

A microbe used in the experiment is *Staphylococcus aureus*, and the number of germs is about 10$^{11}$-10$^{12}$ CFU/m$^3$, and the experiment was conducted in a chamber of 1 m$^3$.

In the chamber where the photocatalytic module was installed, a photocatalytic filter having dimensions of 100 mm×100 mm×10 mm and 6 LEDs radiating ultraviolet light having a peak wavelength of 365 nm were used, and the decrease rate of germs in the air was investigated by radiating ultraviolet light onto the surface of the photocatalytic filter with an average radiation rate of 17.3 mW/cm$^2$ and causing the air to move with a fan.

As a result of the experiment, the photocatalytic module of the present invention showed a sterilization rate of 99% in 60 minutes, while the ionizer exhibited a sterilization rate lower than 90%.

Thus far, exemplary embodiments of the present invention have been described in detail with reference to the accompanying drawings. However, the present invention is not limited to the exemplary embodiments, and it is apparent that modifications and variations can be made within the scope of the present invention. effects of the present invention which are not explicitly described above but are predictable from the configuration of the present invention will be apparent to those skilled in the art from the above descriptions.

The invention claimed is:

1. A photocatalytic module installed in an automobile air conditioner including a duct, the photocatalytic module comprising:
   a duct fixation frame coupled to an inner wall or a joint of the duct to fix the photocatalytic module on the duct, the duct providing a space for an air flowing along a direction;
   a photocatalytic filter including a photocatalytic material on a supporter having cells neighboring one another;
   a filter fixation frame connected to the duct fixation frame on a first side of the duct fixation frame to fix the photocatalytic filter; and
   a spacing member disposed on a second, opposite side to the first side of the duct fixation frame, the spacing member configured to provide a space to accommodate an ultraviolet (UV) light emitting diode (LED) for radiating ultraviolet light toward the photocatalytic filter and having a shape extending along the direction, wherein the spacing member has a first portion extending from the duct fixation frame and a second portion extending from the first portion along another direction perpendicular to the direction, and the photocatalytic module includes a substrate installed on the second portion of the spacing member.

2. The photocatalytic module according to claim 1, wherein the duct fixation frame has an edge surrounding a second space with a shape corresponding to a cross-section of the duct.

3. The photocatalytic module according to claim 2, wherein the photocatalytic filter is fixed to the filter fixation frame while being fitted into the second space of the duct fixation frame.

4. The photocatalytic module according to claim 1, wherein the UV LED has a peak wavelength between 340 nm and 380 nm.

5. The photocatalytic module according to claim 1, further comprising an additional UV LED on the substrate installed on a substrate installation surface and configured to radiate ultraviolet light having a peak wavelength between 260 nm and 280 nm.

6. The photocatalytic module according to claim 5, wherein the additional UV LED is structured to radiate ultraviolet light in an opposite direction that the UV LED radiates ultraviolet light.

7. The photocatalytic module according to claim 1, wherein the UV LED is disposed apart from an air inlet of the duct by a first distance that is shorter than a second distance between the air inlet and the photocatalytic filter.

8. The photocatalytic module according to claim 7, further comprising an additional photocatalytic module installed in the duct and including an additional UV LED for radiating ultraviolet light, wherein the additional UV LED is disposed apart from the air inlet by a third distance greater than the first distance.

9. The photocatalytic module according to claim 1, further comprising an evaporator formed in the duct, wherein the photocatalytic module is placed between an air inlet of the duct and the evaporator.

10. The photocatalytic module according to claim 1, wherein the UV LED is placed to radiate ultraviolet light along the direction of an air flowing in the duct.

11. A photocatalytic module installed in an automobile air conditioner having a duct, comprising:
    a duct fixation frame located adjacent to an inner wall of the duct and structured to fix the photocatalytic module on the duct;
    a filter fixation frame connected to the duct fixation frame at one end of the filter fixation frame at an acute angle with the duct fixation frame;
    a photocatalytic filter fixed by the filter fixation frame and having cells neighboring one another, each cell providing an airflow path and coated with photocatalytic material; and
    a substrate fixed to the duct fixation frame and equipped with an ultraviolet (UV) light emitting diode (LED) for radiating ultraviolet light toward the photocatalytic filter.

12. The photocatalytic module according to claim 11, further comprising:
    a reinforcement frame for connecting the other end of the filter fixation frame to the duct fixation frame and structured to reinforce a rigidity of the filter fixation frame.

13. The photocatalytic module according to claim 11, wherein the photocatalytic filter is fixed to form an acute angle with regard to the duct fixation frame.

14. The photocatalytic module according to claim 13, wherein the acute angle is between 40° and 85°.

15. The photocatalytic module according to claim 11, wherein the UV LED radiates ultraviolet light having a peak wavelength between 340 nm and 380 nm toward the photocatalytic filter.

16. The photocatalytic module according to claim 15, further comprising an additional UV LED installed on the substrate and structured to radiate ultraviolet light having a peak wavelength between 260 nm and 280 nm.

* * * * *